(12) United States Patent
Hibner et al.

(10) Patent No.: US 8,376,957 B2
(45) Date of Patent: Feb. 19, 2013

(54) BIOPSY DEVICE WITH AUXILIARY VACUUM SOURCE

(75) Inventors: John A. Hibner, Mason, OH (US); Trevor W. V. Speeg, Williamsburg, OH (US); Kory A. Gunnerson, Cincinnati, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 306 days.

(21) Appl. No.: 12/709,695

(22) Filed: Feb. 22, 2010

(65) Prior Publication Data

US 2011/0208086 A1  Aug. 25, 2011

(51) Int. Cl.
*A61B 10/00* (2006.01)
(52) U.S. Cl. .......................................... 600/566; 606/45
(58) Field of Classification Search .................. 600/566
See application file for complete search history.

(56) References Cited

U.S. PATENT DOCUMENTS

| | | | |
|---|---|---|---|
| 5,526,822 A | 6/1996 | Burbank et al. | |
| 6,086,544 A | 7/2000 | Hibner et al. | |
| 6,440,086 B1 * | 8/2002 | Hohenberg | 600/567 |
| 6,626,849 B2 | 9/2003 | Huitema et al. | |
| 7,442,171 B2 | 10/2008 | Stephens et al. | |
| 2004/0054299 A1 * | 3/2004 | Burdorff et al. | 600/564 |
| 2006/0074345 A1 | 4/2006 | Hibner | |
| 2007/0032742 A1 | 2/2007 | Monson et al. | |
| 2007/0032743 A1 * | 2/2007 | Hibner | 600/566 |
| 2008/0195066 A1 | 8/2008 | Speeg et al. | |
| 2008/0214955 A1 | 9/2008 | Speeg et al. | |
| 2009/0137928 A1 * | 5/2009 | Quick et al. | 600/566 |
| 2009/0171242 A1 | 7/2009 | Hibner | |
| 2009/0227893 A1 * | 9/2009 | Coonahan et al. | 600/566 |

OTHER PUBLICATIONS

U.S. Appl. No. 12/335,578, filed Dec. 16, 2008, Parihar et al.
U.S. Appl. No. 12/337,874, filed Dec. 18, 2008, Parihar et al.
U.S. Appl. No. 12/337,911, filed Dec. 18, 2008, Parihar et al.
U.S. Appl. No. 12/337,942, filed Dec. 18, 2008, Parihar et al.
U.S. Appl. No. 12/337,997, filed Dec. 18, 2008, Parihar.
U.S. Appl. No. 12/483,305, filed Jun. 12, 2009, Hibner et al.

* cited by examiner

*Primary Examiner* — Max Hindenburg
*Assistant Examiner* — Renee Danega
(74) *Attorney, Agent, or Firm* — Frost Brown Todd LLC

(57) ABSTRACT

A biopsy system comprises a biopsy device, a fluid canister, and an auxiliary vacuum source. The biopsy device comprises a body, a needle, a hollow cutter, and a primary vacuum pump. The primary vacuum pump is operable to induce a vacuum in the lumen of the cutter. The fluid canister is configured to receive liquids communicated proximally through the cutter lumen. The auxiliary vacuum source is operable to induce a vacuum in the cutter lumen, thus supplementing the primary vacuum pump. The auxiliary vacuum source may be coupled directly with the fluid canister, such that the fluid canister is positioned along the fluid path between the auxiliary vacuum source and the biopsy device. The biopsy device may further include an integral tissue sample holder. The cutter lumen, the primary vacuum pump, the fluid canister, and the auxiliary vacuum source are all in fluid communication with the tissue sample holder.

19 Claims, 7 Drawing Sheets

BIOPSY DEVICE WITH AUXILIARY VACUUM SOURCE

BACKGROUND

Biopsy samples have been obtained in a variety of ways in various medical procedures using a variety of devices. Biopsy devices may be used under stereotactic guidance, ultrasound guidance, MRI guidance, PEM guidance, BSGI guidance, or otherwise. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device.

Merely exemplary biopsy devices are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pub. No. 2003/0109803, entitled "MRI Compatible Surgical Biopsy Device," published Jun. 12, 2003; U.S. Pub. No. 2006/0074345, entitled "Biopsy Apparatus and Method," published Apr. 6, 2006; U.S. Pub. No. 2007/0118048, entitled "Remote Thumbwheel for a Surgical Biopsy Device," published May 24, 2007; U.S. Pub. No. 2008/0214955, entitled "Presentation of Biopsy Sample by Biopsy Device," published Sep. 4, 2008; U.S. Pub. No. 2009/0171242, entitled "Clutch and Valving System for Tetherless Biopsy Device," published Jul. 2, 2009; U.S. Non-Provisional patent application Ser. No. 12/335,578, entitled "Hand Actuated Tetherless Biopsy Device with Pistol Grip," filed Dec. 16, 2008; U.S. Non-Provisional patent application Ser. No. 12/337,942, entitled "Biopsy Device with Central Thumbwheel," filed Dec. 18, 2008; and U.S. Non-Provisional patent application Ser. No. 12/483,305, entitled "Tetherless Biopsy Device with Reusable Portion," filed Jun. 12, 2009. The disclosure of each of the above-cited U.S. patents, U.S. patent application Publications, and U.S. Non-Provisional Patent Applications is incorporated by reference herein.

While several systems and methods have been made and used for obtaining a biopsy sample, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1:
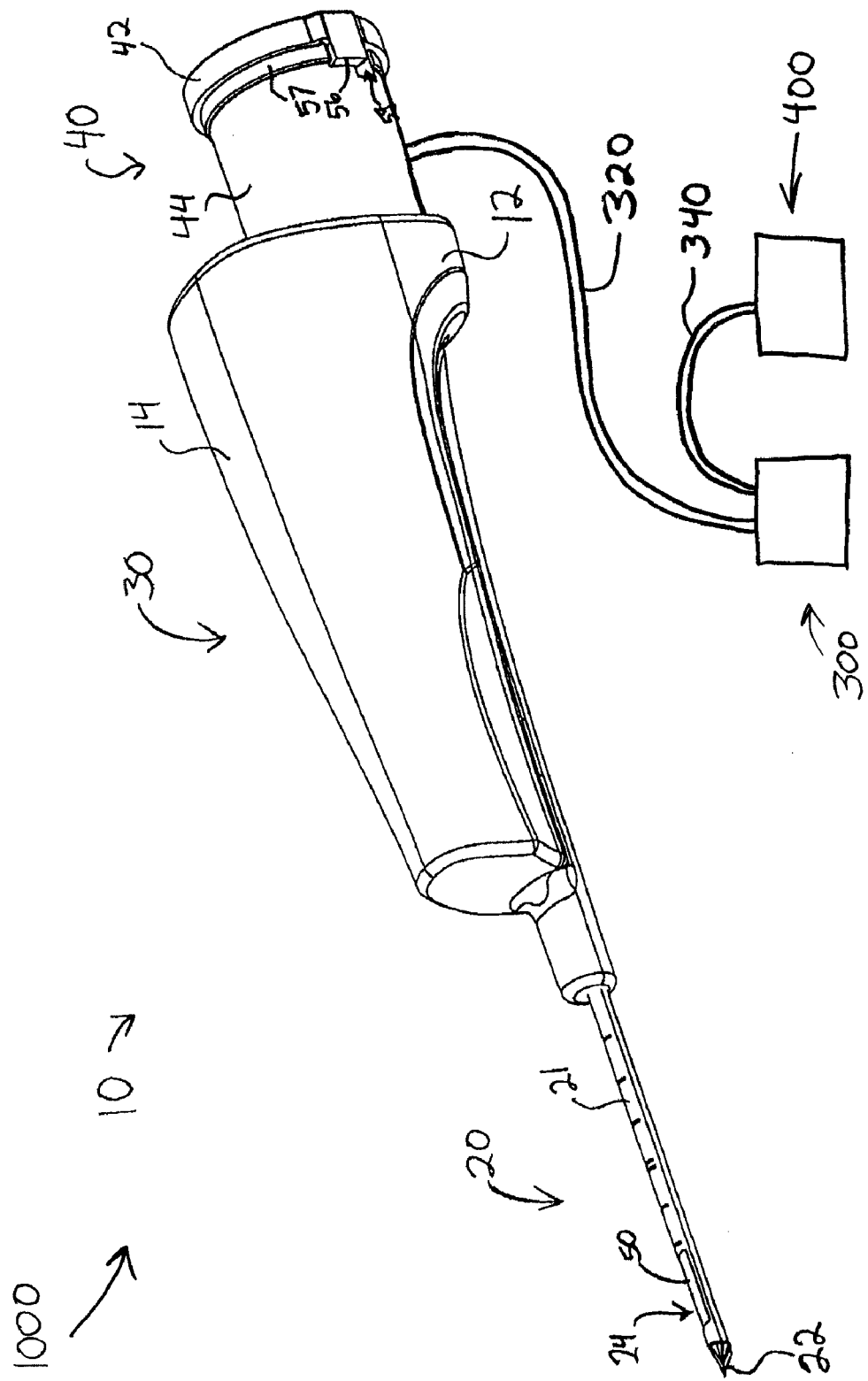
FIG. 1 depicts a perspective view of an exemplary biopsy system including a biopsy device, fluid canister, and auxiliary vacuum source.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Overview

Figure 2:
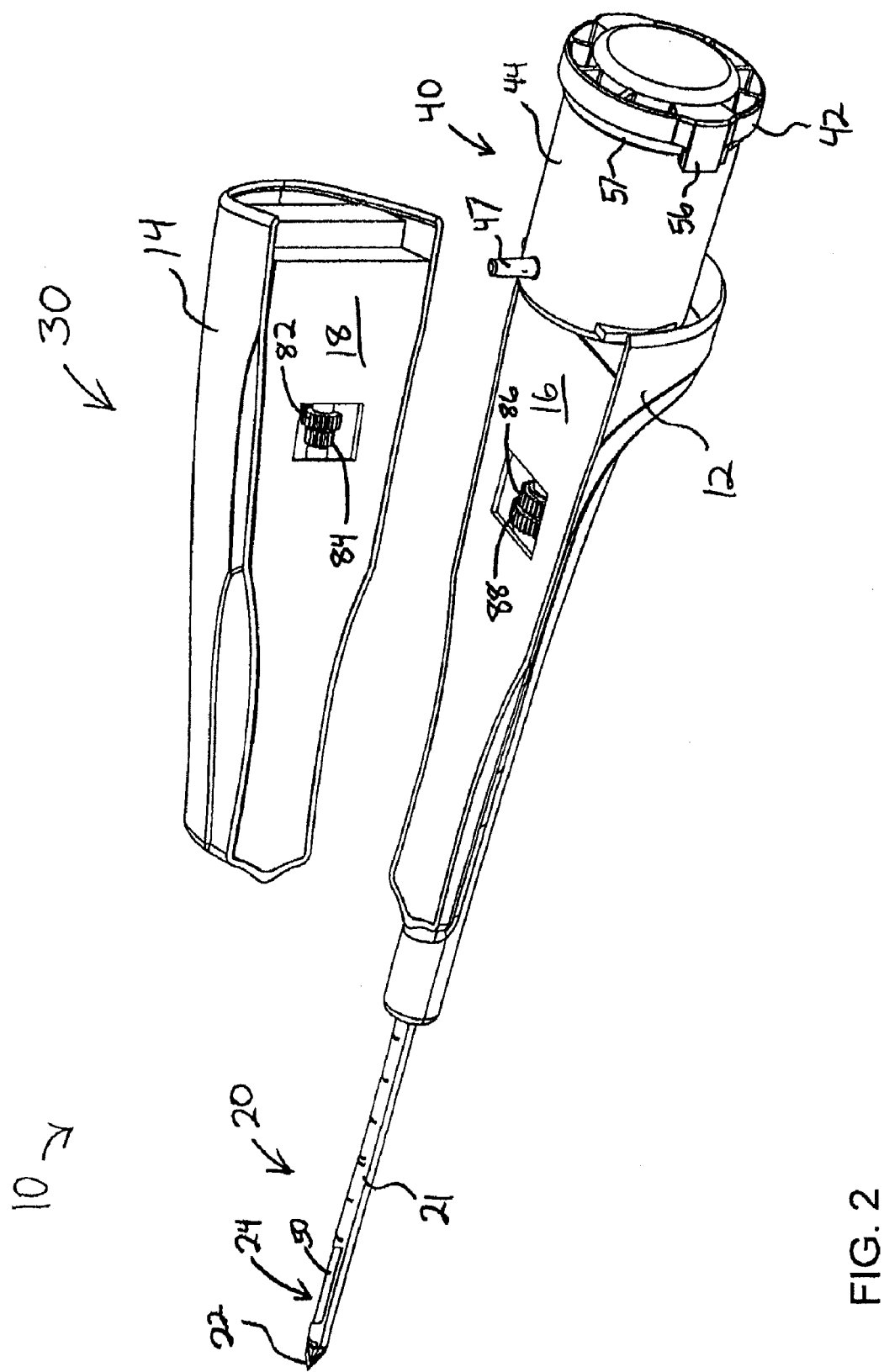
FIG. 2 depicts a perspective view of the biopsy device of the biopsy system of FIG. 1, with a probe portion separated from a holster portion.
Figure 3:
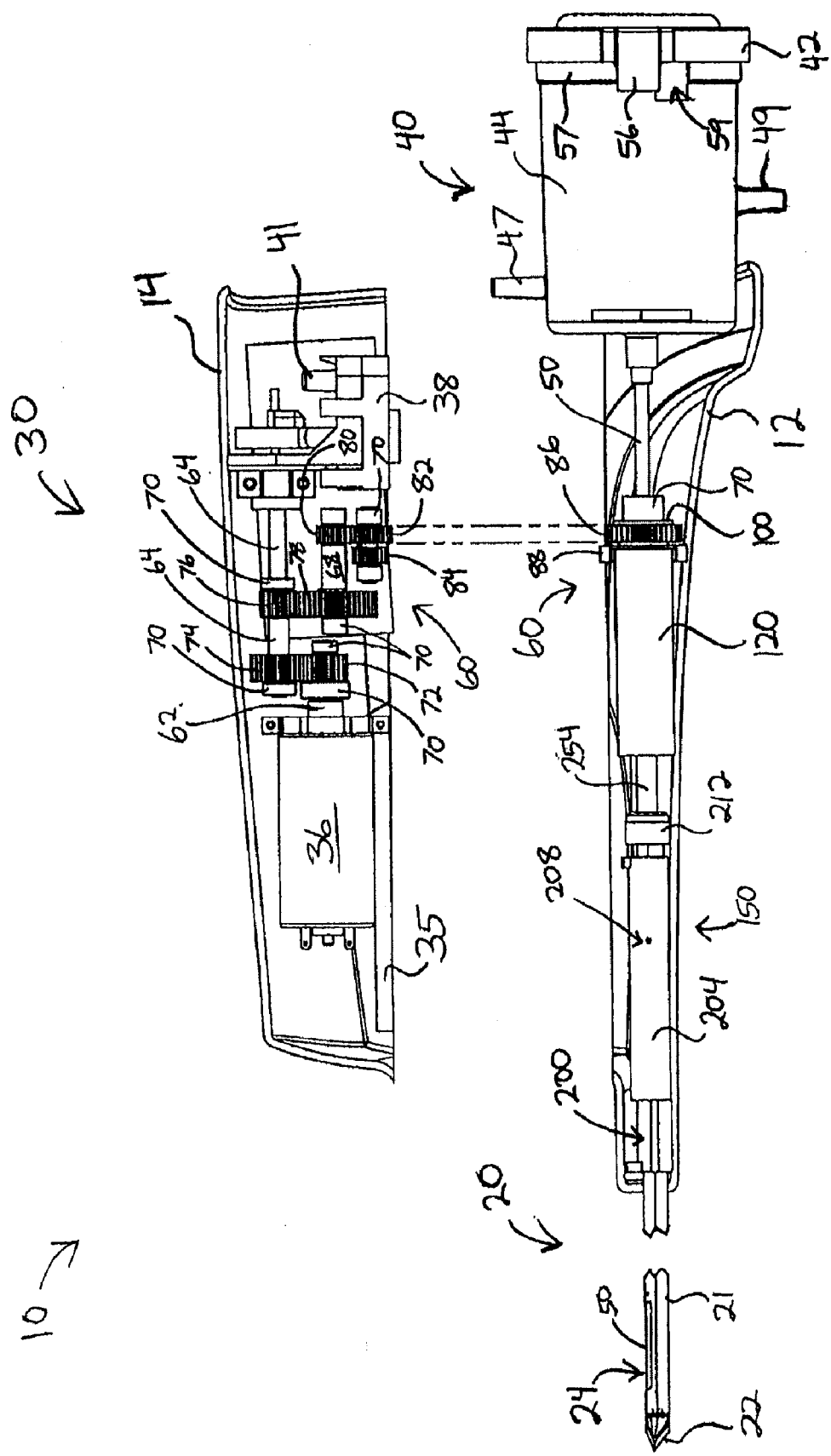
FIG. 3 depicts a side cross-sectional view of the biopsy device of FIG. 2, with the probe portion separated from the holster portion.

As shown in FIG. 1, an exemplary biopsy system (1000) comprises a biopsy device (10), a fluid canister (300), and an auxiliary vacuum source (400). Fluid canister (300) and an auxiliary vacuum source (400) will be described in greater detail below. As shown in FIGS. 1-3, biopsy device (10) of the present example comprises a needle (20), a body (30), and a tissue sample holder (40). In particular, needle (20) extends distally from the distal portion of body (30), while tissue sample holder (40) extends proximally from the proximal portion of body (30). Body (30) is sized and configured such that biopsy device (10) may be operated by a single hand of a user. In particular, and as described in greater detail below, a user may grasp body (30) with a single hand, insert needle (20) into a patient's breast, and collect one or a plurality of tissue samples from within the patient's breast, all with just using a single hand. Alternatively, a user may grasp body (30) with more than one hand and/or with any desired assistance. In some settings, the user may capture a plurality of tissue samples with just a single insertion of needle (20) in the patient's breast. Such tissue samples may be pneumatically deposited in tissue sample holder (40), as described in greater detail below, then retrieved from tissue sample holder (40) for analysis.

Body (30) of the present example comprises a probe (12) and a holster (14). As shown in FIGS. 2-3, and as described in greater detail below, probe (12) is separable from holster (14). In particular, probe (12) and holster (14) may be removably coupled using bayonet mounts (not shown) or any other suitable structures or features. Use of the term "holster" herein should not be read as requiring any portion of probe (12) to be inserted into any portion of holster (14). Indeed, in some variations of biopsy device (10), probe (12) may simply sit on holster (14). In some other variations, a portion of holster (14) may be inserted into probe (12). Furthermore, in some biopsy devices (10), probe (12) and holster (14) may be of unitary or integral construction, such that the two components cannot be separated. By way of example only, in versions where probe (12) and holster (14) are provided as separable components, probe (12) may be provided as a disposable component, while holster (14) may be provided as a reusable component. Still other suitable structural and functional relationships between probe (12) and holster (14) will be apparent to those of ordinary skill in the art in view of the teachings herein.

Some variations of biopsy device (10) may include one or more sensors (not shown), in probe (12) and/or in holster (14), that is/are configured to detect when probe (12) is coupled with holster (14). Such sensors or other features may further be configured to permit only certain types of probes (12) and holsters (14) to be coupled together. In addition or in the alternative, such sensors may be configured to disable one or more functions of probes (12) and/or holsters (14) until a suitable probe (12) and holster (14) are coupled together. Of course, such sensors and features may be varied or omitted as desired.

While examples described herein refer to the acquisition of biopsy samples from a patient's breast, it should be understood that biopsy device (10) may be used in a variety of other procedures for a variety of other purposes and in a variety of other parts of a patient's anatomy.

Exemplary Needle

As shown in FIGS. 1-6, needle (20) of the present example comprises a cannula (21) with a tissue piercing tip (22), a lateral aperture (24), a first lumen (26), and a second lumen (28). Tissue piercing tip (22) is configured to pierce and penetrate tissue, without requiring a high amount of force, and without requiring an opening to be pre-formed in the tissue prior to insertion of tip (22). A cutter (50) is disposed in first lumen (26), and is operable to rotate and translate within first lumen (26) as will be described in greater detail below. Lateral aperture (24) is located proximal to tip (22), is in fluid communication with first lumen (26), and is configured to receive tissue when needle (20) is inserted in a breast and when a cutter (50) is retracted as will also be described in greater detail below. A plurality of openings (27) may provide fluid communication between first and second lumens (26, 28). A plurality of external openings (not shown) may also be formed in needle (20), and may be in fluid communication with second lumen (28). Examples of such external openings are disclosed in U.S. Pub. No. 2007/0032742, entitled "Biopsy Device with Vacuum Assisted Bleeding Control," published Feb. 8, 2007, the disclosure of which is incorporated by reference herein. Of course, as with other components described herein, such external openings are merely optional.

Needle (20) of the present example further comprises a hub (200), as shown in FIGS. 3-6. Hub (200) may be formed of plastic that is overmolded about needle (20) or otherwise secured to needle (20), such that hub (200) is unitarily secured to needle (20). Alternatively, hub (200) may be formed of any other suitable material through any suitable process and may have any other suitable relationship with needle (20).

Figure 4:
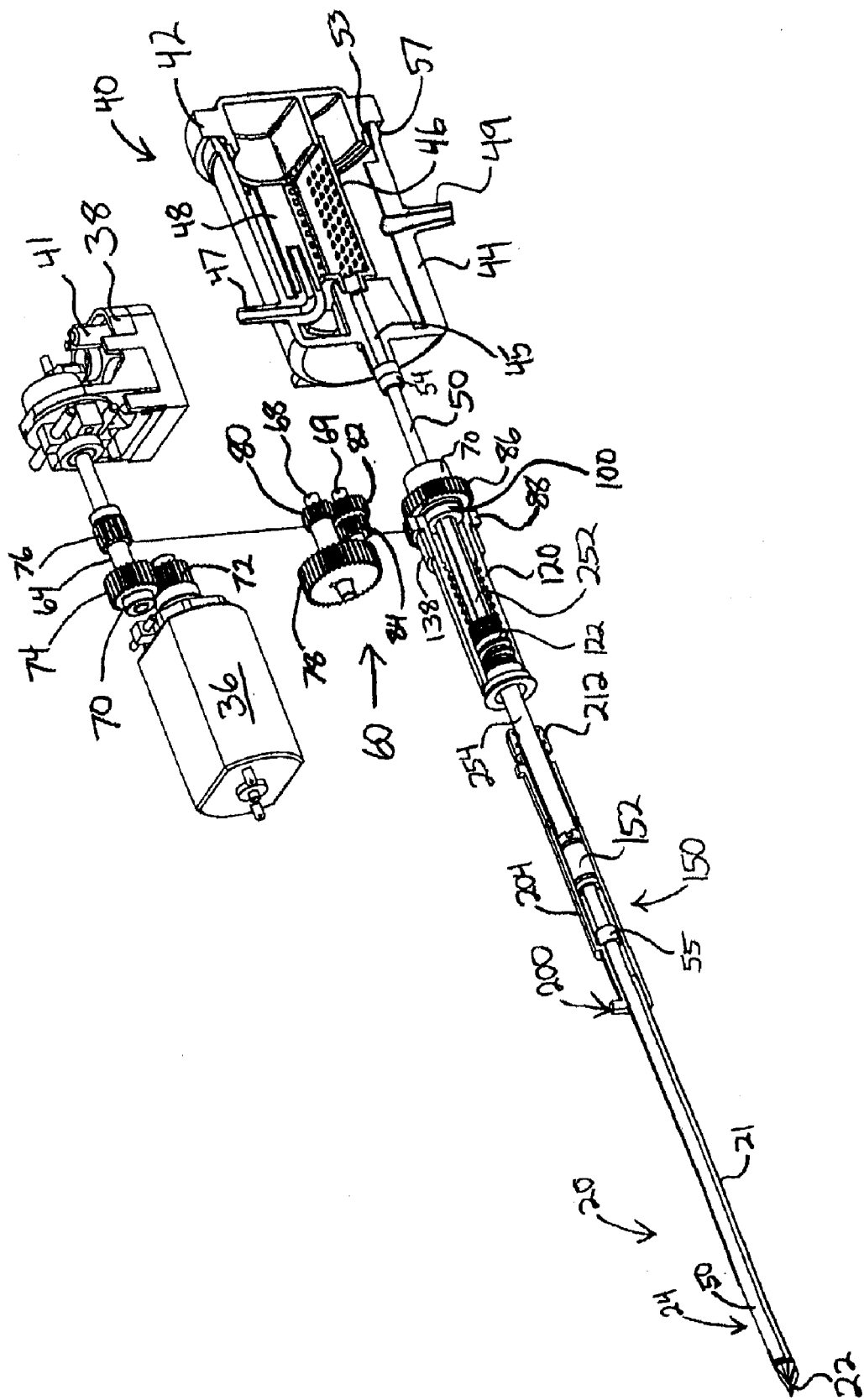
FIG. 4 depicts an exploded view of the biopsy device components of FIG. 3, with portions shown in cross-section, and with a battery and a circuit board removed.
Figure 5:
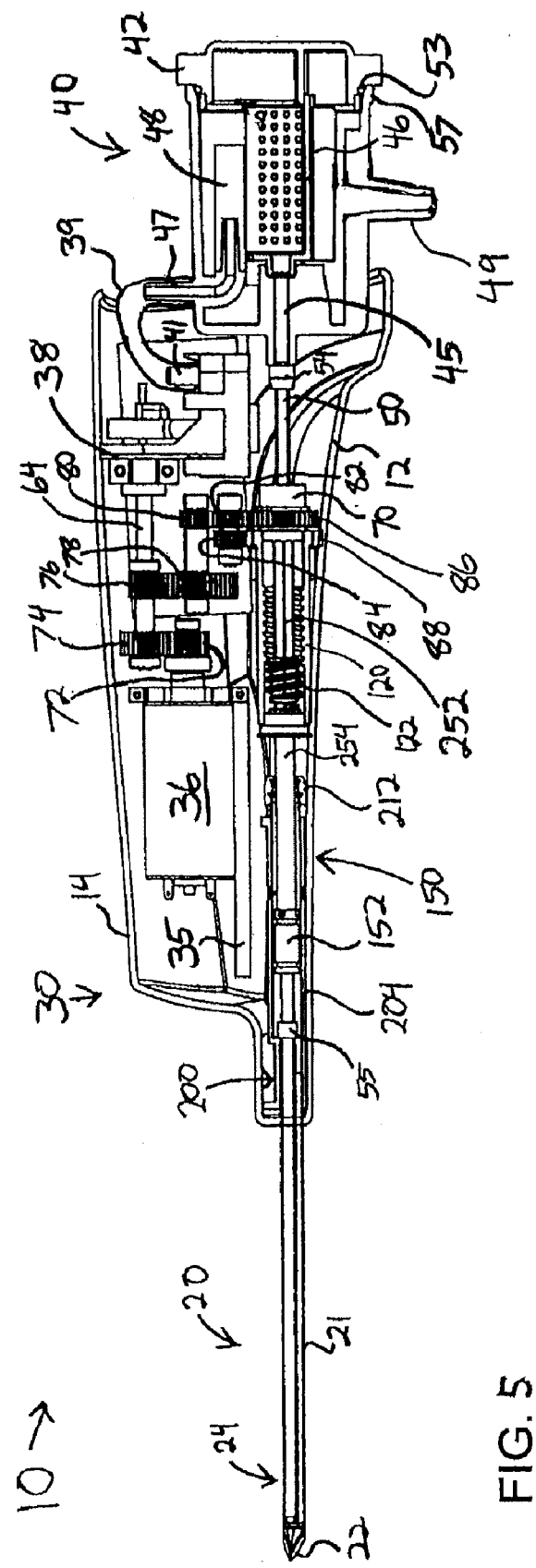
FIG. 5 depicts a side cross-sectional view of the biopsy device of FIG. 2.
Figure 6:
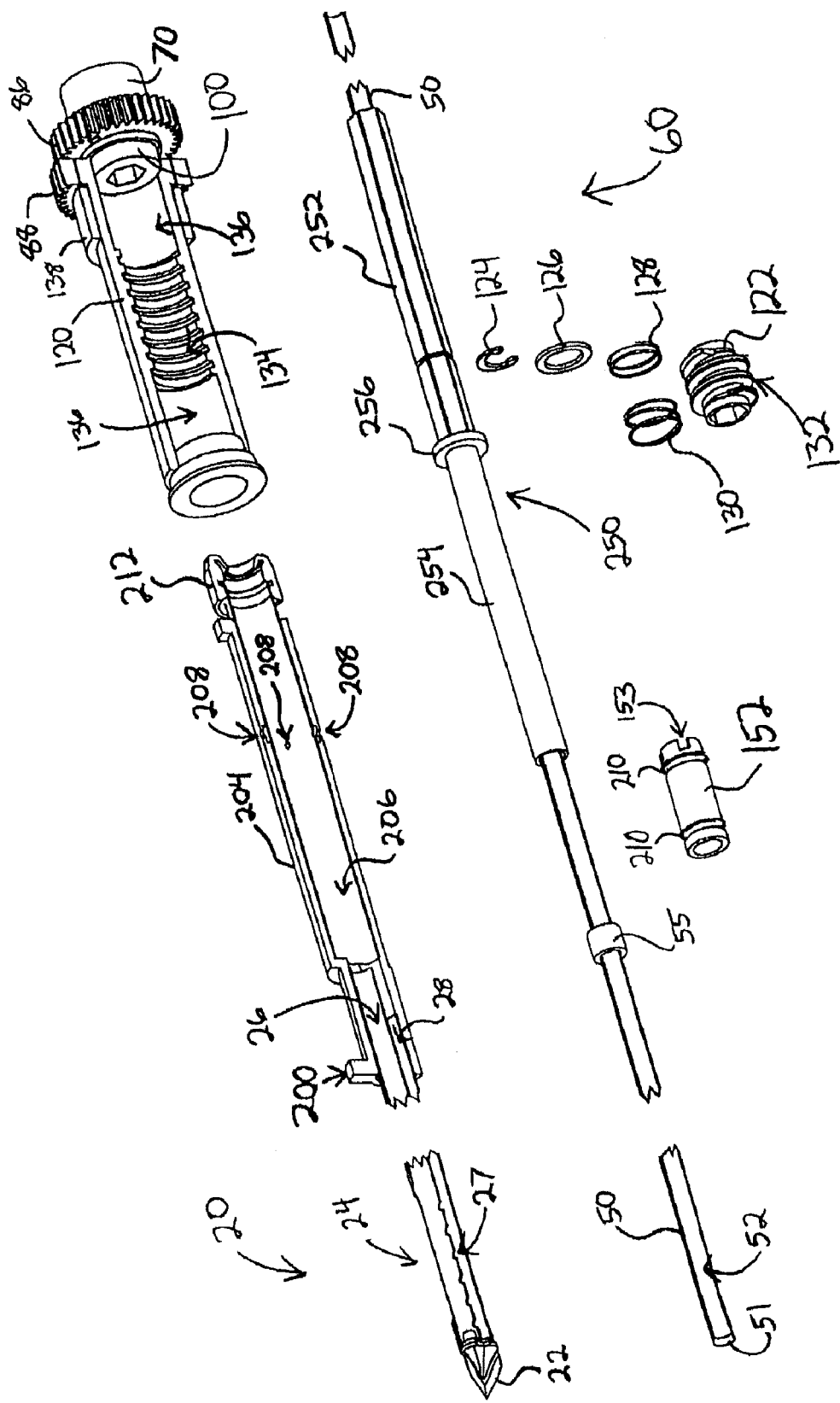
FIG. 6 depicts an exploded view of cutter and needle components of the biopsy device of FIG. 2, with portions shown in cross-section.

Hub (200) of the present example comprises a sleeve portion (204). Sleeve portion (204) extends integrally into probe portion (12) of body (30). As shown in FIGS. 3-5, sleeve portion (204) defines a hollow interior (206), which is in fluid communication with second lumen (28) of needle (20). Sleeve portion (204) also defines a plurality of openings (208), which are radially spaced about the perimeter of sleeve portion (204) at a common longitudinal position, and which are in fluid communication with hollow interior (206). Openings (208) are exposed to ambient air, such that openings (208) provide a vent in the present example. Openings (208) are selectively fluidly coupled with second lumen (28) of needle (20) in this example, as will be described in greater detail below. In particular, openings (208) are selectively coupled with second lumen (28) during use of biopsy device (10), to selectively provide venting to second lumen (28). A pair of o-rings (210) are positioned about a shuttle valve slider (152), to substantially seal second lumen (28) relative to openings (208) when second lumen (28) is not to be vented, depending on the longitudinal position of slider (152) as will be described in greater detail below. A seal (212) is also provided at the proximal end of sleeve (204), at the interface of cutter (50) and sleeve (204). Seal (212) is configured to substantially seal the interface of cutter (50) and sleeve (204), even as cutter (50) rotates and translates relative to sleeve (204). In particular, seal (212) sealingly engages a smooth portion (254) of a sleeve (250) that is unitarily secured to cutter (50). Sleeve (250) further comprises a hex portion (252).

Other suitable features, components, and configurations for needle (20) and hub (200) will be apparent to those of ordinary skill in the art in view of the teachings herein. For instance, needle (20) and/or hub (200) may be configured in accordance with any of the teachings in U.S. Non-Provisional patent application Ser. No. 12/483,305, entitled "Tetherless Biopsy Device with Reusable Portion," filed Jun. 12, 2009, the disclosure of which is incorporated by reference herein. Still other ways in which needle (20) and/or hub (200) may be formed, including alternative techniques, materials, features, components, configurations, functionalities, and operabilities, will be apparent to those of ordinary skill in the art in view of the teachings herein.

Exemplary Body

As noted above, body (30) of the present example comprises a probe portion (12) and a holster portion (14). In the present example, a battery (not shown), a first circuit board (35), a second circuit board (not shown), a motor (36), and a vacuum pump (38) are provided within probe portion (12). The battery may comprise a rechargeable battery, a non-rechargeable battery, or any other type of battery. In other versions, biopsy device (10) is powered by some other source, such as a conventional AC power source or piece of capital equipment, such that the battery is merely optional. The battery is coupled with motor (36) via first circuit board (35), second circuit board (not shown) and a trigger button (not shown) in the present example. The battery may be similar to the battery disclosed in U.S. Non-Provisional patent application Ser. No. 12/483,305, entitled "Tetherless Biopsy Device with Reusable Portion," filed Jun. 12, 2009, the disclosure of which is incorporated by reference herein.

As shown in FIGS. 3-5, motor (36) of the present example is in mechanical communication with vacuum pump (38) and a cutter actuation mechanism (60). In particular, motor (36) is operable to simultaneously activate vacuum pump (38) and cutter actuation mechanism (60) when motor (36) is activated. Alternatively, vacuum pump (38) and cutter rotation mechanism (60) may be activated in any other suitable fashion. By way of example only, vacuum pump (38) and/or cutter rotation mechanism (60) may be activated manually and/or by separate motors and/or in any other suitable fashion. Motor (36) of the present example comprises a conventional DC motor. However, it should be understood that motor (36) may alternatively comprise a pneumatic motor (e.g., with impeller, etc.), a pneumatic linear actuator, an electromechanical linear actuator, or a variety of other types of movement-inducing devices. Various suitable ways in which other types of movement-inducing devices may be incorporated into biopsy device (10) will be apparent to those of ordinary skill in the art in view of the teachings herein.

As shown in FIGS. 3-5, a drive shaft (62) extends from motor (36), and is rotationally driven by motor (36). A pair of bearings (70) and a drive gear (72) are positioned about drive shaft (62). Bearings (70) support drive shaft (62), while drive gear (72) rotates unitarily with drive shaft (62). In particular, motor (36) may be selectively activated to rotate drive shaft (62) and drive gear (72) in either rotational direction. Drive gear (72) meshes with a second gear (74), which is unitarily secured to a second shaft (64). Second shaft (64) also includes associated bearings (70) and a third gear (76). Second shaft (64) and gears (74, 76) rotate unitarily, such that motor (36) is operable to rotatingly drive second shaft (64) and gears (74, 76) via drive shaft (62) and drive gear (72).

Vacuum pump (38) of the present example comprises a conventional diaphragm pump. In particular, a second shaft (64), which is rotationally driven by motor (36) as described above, is coupled with an eccentric disk (not shown—e.g., a device for converting circular motion into rectilinear motion, comprising a disk fixed off-center to second shaft (64)), which is configured to cause a rod (not shown—e.g., the rod may be coupled with or otherwise driven by the eccentric disk) of vacuum pump (38) to reciprocate as motor (36) and shafts (62, 64) rotate. This rod of vacuum pump (38) drives a diaphragm (not shown) of vacuum pump (38) as the rod reciprocates, causing vacuum pump (38) to induce a vacuum. It should be understood that vacuum pump (38) of the present example operates in the same way regardless of which direction motor (36) rotates. Of course, any other suitable type of vacuum pump may be used. Vacuum pump (38) of the present example is operable to induce a vacuum in tissue sample holder (40) when vacuum pump (38) is activated, as will be described in greater detail below. Cutter actuation mechanism (60) is operable to rotate and translate cutter (50) when cutter rotation mechanism (60) is activated, as will also be described in greater detail below. In particular, cutter actuation mechanism (60) is operable to cause cutter (50) to rotate within first lumen (26) and concomitantly cause cutter (50) to translate within first lumen (26), such as to sever a biopsy sample from tissue protruding through lateral aperture (24).

Other suitable, features, components, and configurations for body (30) and its associated components will be apparent to those of ordinary skill in the art in view of the teachings herein. For instance, body (30) and/or one or more components of body (30) may be configured in accordance with any of the teachings in U.S. Non-Provisional patent application Ser. No. 12/483,305, entitled "Tetherless Biopsy Device with Reusable Portion," filed Jun. 12, 2009, the disclosure of which is incorporated by reference herein. Still other ways in which body (30) and/or its associated components may be formed, including alternative techniques, materials, features, components, configurations, functionalities, and operabilities, will be apparent to those of ordinary skill in the art in view of the teachings herein.

Exemplary Valve Mechanism

As shown in FIGS. 3-6, biopsy device (10) also includes a valve mechanism (150) in the present example. Valve mechanism (150) may be similar to the valve mechanism disclosed in U.S. Non-Provisional patent application Ser. No. 12/483, 305, entitled "Tetherless Biopsy Device with Reusable Portion," filed Jun. 12, 2009, the disclosure of which is incorporated by reference herein. Valve mechanism (150) of this example comprises shuttle valve slider (152), o-rings (210), and sleeve (204) of needle hub (200). Shuttle valve slider (152) is positioned coaxially about cutter (50), and is configured to translate relative to sleeve (204) and relative to cutter (50). Shuttle valve slider (152) defines an inner diameter that is greater than the outer diameter defined by cutter (50), such that a gap is provided between the outer diameter of cutter (50) and the inner diameter of shuttle valve slider (152). Such a gap is sufficient to provide longitudinal fluid communication (e.g., atmospheric air, etc.) between the outer diameter of cutter (50) and the inner diameter of shuttle valve slider (152). In addition, the proximal end of shuttle valve slider (152) has notches (153) formed in it, providing an appearance similar to that of a castellated nut or castle nut.

As shown, stop member (55) and shuttle valve slider (152) are configured such that stop member (55) may push shuttle valve slider (152) proximally when stop member (55) is engaged with shuttle valve slider (152); while sleeve (250) and shuttle valve slider (152) are configured such that sleeve (250) may push shuttle valve slider (152) distally when sleeve (250) is engaged with shuttle valve slider (152). However, the distance between the distal end of sleeve (250) and the proximal end of stop member (55) is greater than the length of shuttle valve slider (152), such that there is a degree of "lost motion" between shuttle valve slider (152) and cutter (50) as cutter (50) translates in the present example. Accordingly, shuttle valve slider (152) and the other components of valve mechanism (150) may be configured to allow shuttle valve slider (152) to selectively substantially seal second lumen (28) relative to openings (208) when cutter (50) is in a proximal position and to selectively vent second lumen (28) to atmosphere when cutter (50) is at other positions.

It should be understood that, as with other components described herein, valve mechanism (150) may be varied, modified, substituted, or supplemented in a variety of ways; and that valve mechanism (150) may have a variety of alternative features, components, configurations, and functionalities. Suitable alternative versions, features, components, configurations, and functionalities of valve mechanism (150) will be apparent to those of ordinary skill in the art in view of the teachings herein. By way of example only, valve mechanism (150) and/or any of its components may be configured in accordance with any of the teachings in U.S. Non-Provisional patent application Ser. No. 12/483,305, entitled "Tetherless Biopsy Device with Reusable Portion," filed Jun. 12, 2009, the disclosure of which is incorporated by reference herein.

Exemplary Tissue Sample Holder

As shown in FIGS. 1-6, tissue sample holder (40) of the present example comprises a cap (42), an outer cup (44), and a collection tray (46). Tissue sample holder (40) provides a fluid management system that is configured to facilitate separation of tissue samples from associated fluids as will be described in greater detail below. Cup (44) is secured to probe (12) in the present example. Such engagement may be provided in any suitable fashion (e.g., snap fitting, complementary rigid locking features, etc.). Outer cup (44) of the present example is substantially transparent, allowing the user to view tissue samples on collection tray (46), though outer cup (44) may have any other suitable properties if desired.

Outer cup (44) is in fluid communication with cutter lumen (52) and with vacuum pump (38) in the present example. In particular, outer cup (44) is in fluid communication with cutter lumen (52) via a first port (45); and is in fluid communication with vacuum pump (38) via a second port (47). A conduit (39) couples port (41) of vacuum pump (38) with second port (47) of outer cup (44). A spring-loaded seal (not shown) or other feature may optionally be provided on conduit (39) and/or second port (47) and/or port (41) of vacuum pump (38), to substantially seal tissue sample holder (40)

and/or vacuum pump (38) when conduit (39) is disconnected from tissue sample holder (40) or vacuum pump (38) and/or when probe (12) is decoupled from holster (14). In the present example, second port (47) is further coupled with a hydrophobic filter (48), which is in fluid communication with the interior space defined by outer cup (44). Hydrophobic filter (48) is configured to permit vacuum pump (38) to induce a vacuum in tissue sample holder (40) while preventing liquids from being communicated from tissue sample holder (40) to vacuum pump (38). In addition to or in lieu of having hydrophobic filter (48) a highly absorbent material (e.g., hydrophilic member) may be provided in tissue sample holder (40) to soak up liquids. Alternatively, liquids may be dealt with in any other suitable fashion. As described in greater detail below, the vacuum created in tissue sample holder (40) by vacuum pump (38) is communicated to cutter (50) in the present example. In particular, vacuum pump (38) may be used to induce a vacuum in cutter lumen (52); with such a vacuum being communicated through conduit (39), ports (41, 45, 47), and the interior of outer cup (44).

As shown in FIG. 1, outer cup (44) is also in fluid communication with fluid canister (300), which is further in fluid communication with auxiliary vacuum source (400). In particular, and as shown in FIGS. 3-5, outer cup (44) includes a third port (49). A conduit (320) is coupled with third port (49) and with fluid canister (300), such that conduit (320) provides fluid communication from outer cup (44) to fluid canister (300). Conduit (320) may comprise a flexible tube or other type of structure. As will be described in greater detail below, fluid canister (300) is coupled with auxiliary vacuum source (400) via a conduit (340), such that conduit (340) provides fluid communication from auxiliary vacuum source (400). Thus, a vacuum generated by auxiliary vacuum source (400) may be communicated to outer cup (44) via conduits (320, 340) and via vacuum canister (300). It should be understood that the vacuum created in tissue sample holder (40) by auxiliary vacuum source (400) is further communicated to cutter (50) in the present example. In particular, auxiliary vacuum source (400) may be used to induce a vacuum in cutter lumen (52); with such a vacuum being communicated through conduits (320, 340), vacuum canister (300), ports (45, 49), and the interior of outer cup (44). Auxiliary vacuum source (400) may therefore provide a vacuum supplementing or substituting the vacuum provided by vacuum pump (38).

Fluids communicated to outer cup (44) (e.g., bodily fluids and/or saline communicated proximally through cutter lumen (52), etc.) may drain into fluid canister (300), which may collect such fluids during the course of one or more tissue sampling procedures. A spring-loaded seal (not shown), removable cap (not shown), and/or other feature may optionally be provided on third port (49), to substantially seal third port (49) when conduit (320) is disconnected from tissue sample holder (40). For instance, fluid canister (300) or auxiliary vacuum source (400) may be unnecessary or undesired in some settings. Allowing third part (49) to be selectively substantially sealed may thus allow the user to operate biopsy device (10) in a manner where biopsy device (10) is completely "untethered" to external components such as fluid canister (300) or auxiliary vacuum source (400). It should therefore be understood that fluid canister (300) and auxiliary vacuum source (400) are each merely optional components. Biopsy device (10) may be used with both fluid canister (300) and auxiliary vacuum source (400); with just one of fluid canister (300) or auxiliary vacuum source (400); or with neither of fluid canister (300) or auxiliary vacuum source (400). Fluid canister (300) and auxiliary vacuum source (400) will be described in greater detail below.

Cap (42) is removably coupled with outer cup (44) in the present example. A pair of latches (56) provide selective engagement between cap (42) and outer cup (44). In particular, latches (56) engage a lip (57) of outer cup (44). Lip (57) has gaps (59) permitting passage of latches (56), such that a user may secure cap (42) to outer cup (44) by aligning latches (56) with gaps (59), pushing cap (42) onto outer cup (44), then rotating cap (42) past gaps (59) to engage latches (56) with lip (57). Alternatively, cap (42) may be secured to outer cup (44) in any other suitable fashion. An o-ring (53) provides a seal when cap (42) is engaged with outer cup (44). A vacuum may thus be maintained within outer cup (44) when cap (42) is secured to outer cup (44). In operation, a user may remove cap (42) to access tissue samples that have gathered on collection tray (46) during a biopsy process. In the present example, cap (42) is removed by rotating cap (42) to align latches (56) with gaps (59), then pulling cap (42) off. Of course, cap (42) may be removed from outer cup (44) in any other suitable fashion.

Tissue sample holder (40) of the present example is configured to hold at least ten tissue samples. Alternatively, tissue sample holder (40) may be configured to hold any other suitable number of tissue samples. It should be understood that, as with other components described herein, tissue sample holder (40) may be varied, modified, substituted, or supplemented in a variety of ways; and that tissue sample holder (40) may have a variety of alternative features, components, configurations, and functionalities. For instance, tissue sample holder (40) may be alternatively configured such that it has a plurality of discrete tissue sample compartments that may be selectively indexed to cutter lumen (52). Such indexing may be provided automatically or manually. By way of example only, tissue sample holder (40) may be configured and operable in accordance with the teachings of U.S. Pub. No. 2008/0195066, entitled "Revolving Tissue Sample Holder for Biopsy Device," published Aug. 14, 2008, the disclosure of which is incorporated by reference herein; U.S. Non-Provisional patent application Ser. No. 12/337,997, entitled "Tissue Biopsy Device with Rotatably Linked Thumbwheel and Tissue Sample Holder," filed Dec. 18, 2008; U.S. Non-Provisional patent application Ser. No. 12/337,911, entitled "Biopsy Device with Discrete Tissue Chambers," filed Dec. 18, 2008, the disclosure of which is incorporated by reference herein; or U.S. Non-Provisional patent application Ser. No. 12/337,874, entitled "Mechanical Tissue Sample Holder Indexing Device," filed Dec. 18, 2008, the disclosure of which is incorporated by reference herein. Other suitable alternative versions, features, components, configurations, and functionalities of tissue sample holder (40) will be apparent to those of ordinary skill in the art in view of the teachings herein. Alternatively, tissue sample holder (40) may simply be omitted, if desired.

Exemplary Cutter

As shown in FIGS. 1-6, cutter (50) of the present example is substantially hollow, such that cutter (50) defines a cutter lumen (52). Cutter (50) also has a substantially sharp distal edge (51), such that cutter (50) is operable to sever a biopsy sample from tissue protruding through lateral aperture (24) of needle (20). Alternatively, the distal end of cutter (50) may have any other suitable configuration. As shown in FIGS. 3-5, a proximal portion of cutter (50) extends into tissue sample holder (40). A vacuum created in tissue sample holder (40) by vacuum pump (38) and/or by auxiliary vacuum source (400) is thus communicated to cutter lumen (52). A seal (54) is provided at the interface of cutter (50) and outer cup (44). Seal (54) is configured to substantially seal the interface of cutter (50) and outer cup (44), even as cutter (50) rotates and translates relative to outer cup (44). Furthermore, cutter (50) is configured such that it remains in sealed fluid communication with the interior of tissue sample holder (40) even when cutter (50) is in a distal most position. For instance, the length of cutter (50) may be such that at least a portion of cutter (50) is always disposed in outer cup (44) of tissue sample holder (40) during operation of biopsy device (10). Of course, cutter (50) may have any other suitable alternative features or configurations. Similarly, cutter (50) may have any other suitable alternative relationships with tissue sample holder (40).

It should be understood that, as with other components described herein, cutter (50) may be varied, modified, substituted, or supplemented in a variety of ways; and that cutter (50) may have a variety of alternative features, components, configurations, and functionalities. Suitable alternative versions, features, components, configurations, and functionalities of cutter (50) will be apparent to those of ordinary skill in the art in view of the teachings herein. By way of example only, cutter (50) and/or one of its components may be configured in accordance with any of the teachings in U.S. Non-Provisional patent application Ser. No. 12/483,305, entitled "Tetherless Biopsy Device with Reusable Portion," filed Jun. 12, 2009, the disclosure of which is incorporated by reference herein.

Exemplary Cutter Actuation Mechanism

In the present example, cutter actuation mechanism (60) and its components are configured in accordance with the teachings of the cutter actuation mechanism and components disclosed in U.S. Non-Provisional patent application Ser. No. 12/483,305, entitled "Tetherless Biopsy Device with Reusable Portion," filed Jun. 12, 2009, the disclosure of which is incorporated by reference herein. In particular, and as shown in FIGS. 3-5, cutter actuation mechanism (60) of the present example comprises motor (36), shafts (62, 64, 68, 69), gears (72, 74, 76, 78, 80, 82, 84), and bearings (70), each of which are contained within holster (14) in the present example. In the present example, activation of motor (36) will rotate gears (82, 84). As shown in FIG. 2, gears (82, 84) are partially exposed by an opening formed in a cover plate (18) of holster (14) in the present example.

Cutter actuation mechanism (60) of the present example further comprises a hex nut (100) and a worm nut (120). Worm nut (120) is supported by a bushing (138). Hex nut (100) includes a gear (86), which is configured to rotate unitarily with hex nut (100). Worm nut (120) also includes a gear (88), which is configured to rotate unitarily with worm nut (120). Gear (86) is configured to mesh with gear (82) when probe (12) and holster (14) are coupled together; while gear (88) is configured to mesh with gear (84) when probe (12) and holster (14) are coupled together. In particular, and as shown in FIG. 2, gears (86, 88) are partially exposed by an opening formed in a cover plate (16) of probe (12) in the present example. Motor (36) is thus operable to rotatingly drive gears (86, 88) in the present example when probe (12) and holster (14) are coupled together. Such rotation of gears (86, 88) will cause cutter (50) to rotate and translate simultaneously in the present example.

Gear (86) of hex nut (100) is configured to mesh with gear (82), such that rotation of gear (82) causes rotation of hex nut (100). Such rotation of hex nut (100) will cause corresponding rotation of cutter (50). It will therefore be understood that cutter actuation mechanism (60) may cause rotation of cutter (50) in response to activation of motor (36), with rotation of motor (36) being communicated to cutter (50) through shafts (62, 64, 68, 69), gears (72, 74, 76, 78, 80, 82, 84, 86), hex nut (100), and sleeve (250). Of course, any other suitable structures, components, configurations, or techniques may be used to provide rotation of cutter (50).

Gears (82, 84) of holster (14) rotate simultaneously when motor (36) is activated. As noted above, gears (82, 84) mesh with gears (86, 88) of probe (12) when probe (12) is coupled with holster (14), such that activated motor (36) rotates gears (86, 88) simultaneously. Activated motor (36) will thus rotate hex nut (100) and worm nut (120) simultaneously. It should therefore be understood that sleeve (250), cutter (50), lead screw (122), and worm nut (120) will all rotate simultaneously when motor (36) is activated. It will therefore be understood that the simultaneous rotation of sleeve (250), cutter (50), lead screw (122), and worm nut (120) will provide translation of cutter (50) in response to activation of motor (36). Of course, any other suitable structures, components, configurations, or techniques may be used to provide translation of cutter (50).

In the present example, cutter (50) is retracted proximally when motor (36) is activated to rotate cutter (50) counterclockwise (viewed from tissue sample holder (40) toward needle (20)); while cutter (50) is advanced distally when motor (36) is activated to rotate cutter (50) clockwise (viewed from tissue sample holder (40) toward needle (20)). The direction of motor (36) rotation may thus be reversed to transition between distal and proximal translation of cutter (50). Alternatively, cutter actuation mechanism (60) may be configured to be self-reversing, such that cutter (50) may be translated distally and proximally without reversing the direction of motor (36) rotation.

In one merely illustrative example of operation of cutter actuation mechanism (100), cutter (50) may be initially located in a distal-most position, such that lateral aperture (24) is "closed"; with lead screw (122) being positioned at the distal smooth section (136) of worm nut (120). Spring (130) biases lead screw (122) proximally to engage threads (132) with threads (134). At this stage, clockwise rotation of cutter (50) relative to worm nut (120) will not result in any translation of cutter (50) (e.g., lead screw (122) will essentially "freewheel"); while counterclockwise rotation of cutter (50) relative to worm nut (120) will result in proximal translation of cutter (50). As cutter (50) is rotated by motor (36) and cutter actuation mechanism (60) in the counterclockwise direction (viewed from tissue sample holder (40) toward needle (20)), cutter actuation mechanism (100) causes cutter (50) to retract proximally. As noted above, such proximal or rearward translation may be effected through engagement of threads (132, 134), and due to lead screw (122) rotating at a faster speed than worm nut (120). Lead screw (122) continues to traverse threads (134) of worm nut (120) as cutter (50) continues to retract proximally.

Cutter (50) then reaches a proximal-most position, such that lateral aperture (24) is "opened". At this stage, lead screw (122) is positioned at the proximal smooth section (136) of worm nut (120). Spring (128) biases lead screw (122) distally to engage threads (132) with threads (134). At this stage, continued counterclockwise rotation of cutter (50) relative to worm nut (120) will not result in any translation of cutter (50) (e.g., lead screw (122) will essentially "freewheel"); while clockwise rotation of cutter (50) relative to worm nut (120) will result in distal translation of cutter (50). To that end, motor (36) may again be activated, with its rotation direction being reversed to reverse the rotation direction of cutter (50) and associated components. In particular, reversing the rotational direction of motor (36) causes cutter (50) to rotate clockwise (viewed from tissue sample holder (40) toward needle (20)). Such clockwise rotation of cutter (50) causes cutter to advance distally to reach the distal-most position again.

While cutter (50) is shown and described above as rotating counterclockwise (viewed from tissue sample holder (40) toward needle (20)) during retraction of cutter (50) and clockwise (viewed from tissue sample holder (40) toward needle (20)) during advancement of cutter (50), it should be immediately apparent to those of ordinary skill in the art that cutter (50) may instead be rotated clockwise during retraction of cutter (50) and counterclockwise during advancement of cutter. For instance, such reversal may be provided by reversing the orientation of threads (132, 134). Alternatively, such reversal may be provided by changing the differential such that worm nut (120) rotates faster than cutter (50). Of course, any other suitable structures, components, configurations, or techniques may be used to provide translation and/or rotation of cutter (50). It should therefore be understood that, as with other components described herein, cutter actuation mechanism (60) may be varied, modified, substituted, or supplemented in a variety of ways; and that cutter actuation mechanism (60) may have a variety of alternative features, components, configurations, and functionalities. By way of example only, biopsy device (10) may be configured such that cutter (50) does not translate (e.g., such that cutter (50) merely rotates, etc.); or such that cutter (50) does not rotate (e.g., such that cutter (50) merely translates, etc.). Other suitable alternative versions, features, components, configurations, and functionalities of cutter actuation mechanism (60) will be apparent to those of ordinary skill in the art in view of the teachings herein.

Exemplary Fluid Canister

Figure 7:
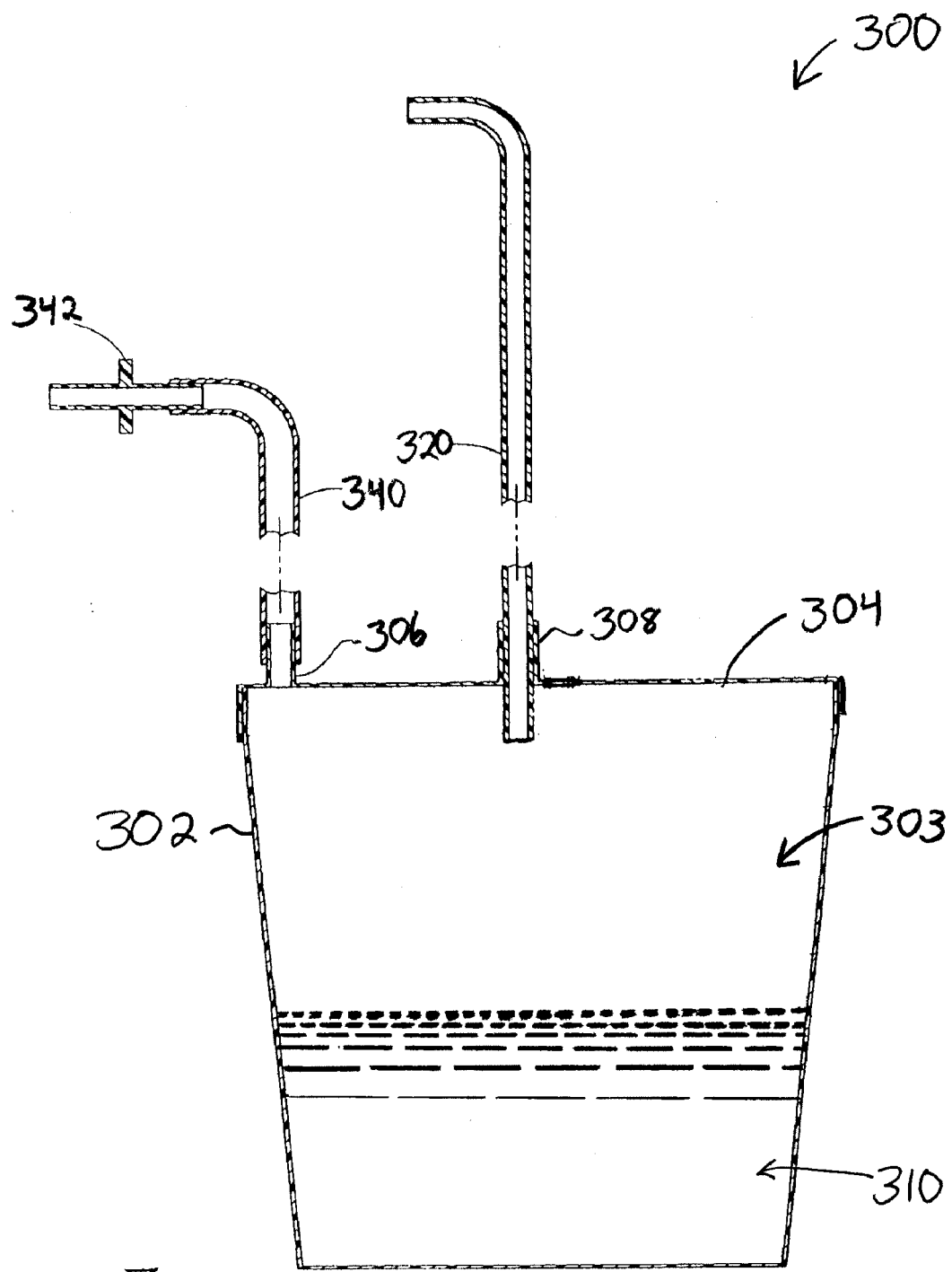
FIG. 7 depicts a side cross-sectional view of the fluid canister of the biopsy system of FIG. 1.

As noted above, in some versions of biopsy system (1000), tissue sample holder (40) of biopsy device (10) is coupled with fluid canister (300) via conduit (320). Fluid canister (300) may comprise a conventional fluid canister (300). As shown in FIG. 7, fluid canister (300) of the present example comprises a cup (302) and a lid (304). Cup (302) defines a hollow interior (303) that is configured to receive liquid (320), such that cup (302) is configured to collect and contain liquid (320). Cup (302) may be substantially transparent or translucent, allowing a user to see an amount of liquid (320) in cup (302) with relative ease. Cup (302) may also include visual indicia to indicate the volume of fluid contained within cup (302). In addition or in the alternative, cup (302) may include a marking indicating a fluid level at which cup (302) needs to be emptied, etc. Lid (304) is configured to engage cup (302), such that lid (304) may form a fluid tight seal with cup (302).

Lid (304) of the present example comprises a first port (308) and a second port (306). First port (308) is coupled with conduit (320); while second port (306) is coupled with conduit (340). In the present example, first port (308) extends upwardly from lid (304) and is configured to insertingly receive conduit (320), such that conduit (320) is inserted into first port (308). Alternatively, first port (308) and conduit (320) may be configured such that first port (308) is inserted into conduit (320). Other suitable ways in which fluid canister (300) may be coupled with conduit (320) will be apparent to those of ordinary skill in the art in view of the teachings herein. It should also be understood that first port (308) may include a check valve (not shown), duckbill seal, spring-loaded seal (not shown), removable cap (not shown), and/or other feature that is configured to substantially seal first port (308) when conduit (320) is disconnected from lid (304). Such a feature may substantially prevent accidental spillage of fluid (310) from fluid canister (300) when conduit (320) is disconnected from lid (304) (e.g., during transport of fluid canister (300) after a biopsy procedure, etc.).

Conduit (340) of the present example comprises a flexible tube, though any other suitable type of structure may be used. Second port (306) extends upwardly from lid (304) in the present example; and is configured to be insertingly received by conduit (340) such that second port (306) is inserted into conduit (340). Alternatively, second port (306) and conduit (340) may be configured such that conduit (340) is inserted into second port (306). Other suitable ways in which fluid canister (300) may be coupled with conduit (340) will be apparent to those of ordinary skill in the art in view of the teachings herein. It should also be understood that second port (306) may include a check valve (not shown), duckbill seal, spring-loaded seal (not shown), removable cap (not shown), and/or other feature that is configured to substantially seal second port (306) when conduit (340) is disconnected from lid (304). Such a feature may further substantially prevent accidental spillage of fluid (310) from fluid canister (300) when conduit (340) is disconnected from lid (304) (e.g., during transport of fluid canister (300) after a biopsy procedure, etc.).

As is also shown in FIG. 7, a hydrophobic filter (342) is coupled with conduit (340) in the present example. While not shown in FIG. 7, it should be understood that another conduit (340) may be coupled with hydrophobic filter (342) to provide fluid communication from auxiliary vacuum source (400) to fluid canister (300). Of course, to the extent that a hydrophobic filter (342) is even used (hydrophobic filter (342) is not necessary in all versions per se), hydrophobic filter (342) may alternatively be incorporated into second port (306), into a part of auxiliary vacuum source (400), or at any other suitable location within biopsy system (1000). Hydrophobic filter (342) is configured to permit auxiliary vacuum source (400) to induce a vacuum in fluid canister (300) while preventing liquid (310) from being communicated from fluid canister (300) to auxiliary vacuum source (400). In addition to or in lieu of having hydrophobic filter (342) a highly absorbent material may be provided in cup (302) to soak up liquid (310). Alternatively, liquids may be dealt with in any other suitable fashion.

As described elsewhere herein, fluid canister (300) may essentially act as a relay between auxiliary vacuum source (400) and tissue sample holder (40) of biopsy device (10), such that a vacuum induced by auxiliary vacuum source (400) may induce a vacuum in tissue sample holder (40) (and, hence, in cutter lumen (52), etc.) via fluid canister (300). Furthermore, fluid canister (300) may act as a reservoir for liquids (310) that are communicated proximally through cutter lumen (52), such that fluid canister (300) provides drainage of outer cup (44) via port (49) and conduit (320). Thus, the excess fluid capacity provided by fluid canister (300), beyond the fluid capacity that would otherwise be provided by only outer cup (44), may allow biopsy system (1000) to be used in settings where significant amounts of liquid (310) may need to be handled. The use of fluid canister (300) may also permit the fluid capacity of outer cup (44) to be less than it might otherwise be, which may in turn allow the size of tissue sample holder (40) to be reduced.

As another merely illustrative variation, a hydrophilic member (not shown) or other type of absorbent member may be positioned within hollow interior (303) of cup (302) to soak up liquids communicated through conduit (320). Such a hydrophilic member may swell and reduce the effective internal volume of cup (302) as the hydrophilic member absorbs liquids, which may in turn allow auxiliary vacuum source (400) to generate and maintain a vacuum within outer cup (44) more easily.

While biopsy system (1000) of the present example includes both fluid canister (300) and auxiliary vacuum source (400), it should be understood that the components of biopsy system (1000) may be arranged and used in various other permutations. For instance, and as noted above, biopsy device (10) may simply be used by itself, without conduit (320) or conduit (340) being coupled with biopsy device (10). Fluid canister (300) and auxiliary vacuum source (400) may both thus be omitted in some versions. Port (49) may include a sealing feature or cap to accommodate such arrangements; or port (49) may be simply omitted. As another merely illustrative example, some versions of biopsy system (1000) may include just fluid canister (300) without also including auxiliary vacuum source (400). For instance, vacuum pump (38) and/or some other source of vacuum may be used to generate a vacuum within tissue sample holder (40); and liquids may drain from tissue sample holder into fluid canister (300) under the influence of gravity or in any other suitable fashion. Other suitable arrangements of components for biopsy system (1000) will be apparent to those of ordinary skill in the art in view of the teachings herein.

Exemplary Auxiliary Vacuum Source

As noted above, in some versions of biopsy system (1000) fluid canister (300) is coupled with auxiliary vacuum source (400) via conduit (340), with an optional hydrophobic filter (342) being provided along the fluid path of conduit (340). Auxiliary vacuum source (400) may comprise a conventional vacuum pump (not shown) and any other suitable components as will be apparent to those of ordinary skill in the art in view of the teachings herein. As also noted above, a vacuum generated by auxiliary vacuum source (400) may be communicated to cutter lumen (52) via conduits (320, 340), fluid canister (300), tissue sample holder (40), and ports (45, 49, 306, 308). In some versions, auxiliary vacuum source (400) is used to supplement a vacuum that is already being provided by vacuum pump (38). Auxiliary vacuum source (400) and vacuum pump (38) may thus be operated simultaneously. Furthermore, auxiliary vacuum source (400) may be configured such that it is activated automatically upon activation of vacuum pump (38). Various suitable ways in which such automatic/simultaneous activation may be provided will be apparent to those of ordinary skill in the art in view of the teachings herein.

In some versions, auxiliary vacuum source (400) is activated independently of vacuum pump (38). For instance, a foot pedal switch (not shown) or some other type of activation feature may be coupled with auxiliary vacuum source (400) to provide selective activation of auxiliary vacuum source (400). Thus, in some such versions, vacuum pump (38) may provide the sole source of vacuum until the user determines that additional vacuum is warranted, in which case the user may selectively activate auxiliary vacuum source (400) to provide such additional vacuum. Auxiliary vacuum source (400) may thus be selectively activated in the middle of a biopsy procedure (or at the beginning of a biopsy procedure or at any other suitable time). It should also be understood that vacuum pump (38) may even be omitted in some versions, such that auxiliary vacuum source (400) is the sole source of vacuum.

While auxiliary vacuum source (400) communicates a vacuum to biopsy device (10) via fluid canister (300) in the present example, it should be understood that auxiliary vacuum source (400) may alternatively bypass fluid canister (300) if desired. For instance, outer cup (44) of tissue sample holder (40) may include a fourth port (not shown) that is configured to couple with a conduit (not shown) that is also coupled with auxiliary vacuum source (400). Such a fourth port may include a hydrophobic filter to prevent liquids from being communicated from tissue sample holder (40) to auxiliary vacuum source (400). In some such versions, fluid canister (300) may simply receive liquid (310) under the influence of gravity, without the assistance of a vacuum to draw liquid (310) into fluid canister (300). Of course, some permutations of biopsy system (1000) components may include the omission of fluid canister (300) altogether. For instance, third port (49) may be coupled directly with auxiliary vacuum source (400) via a conduit.

As another merely illustrative variation of biopsy system (1000) (e.g., those where auxiliary vacuum source (400) is coupled with a fourth port of tissue sample holder (40) and/or where the vacuum source is internally within body (30), etc.), conduit (320) may comprise a flexible tube (e.g., with a length between approximately three inches and approximately twelve inches, etc.), with one end coupled with third port (49) and the other end being capped/sealed. Fluid canister (300) is omitted in some such versions. It should be understood that such a capped/sealed flexible tube may itself provide a volumetric extension of outer cup (44), such that excess fluids may be drained from outer cup (44) into the capped/sealed flexible tube. It should also be understood that the weight of fluid within such a capped/sealed flexible tube, along with the flexibility of such a tube, may substantially keep fluids within the tube at a height level that is below the height level of outer cup (44) as biopsy device (10) is rotated about the longitudinal axis defined by needle (20). For instance, such a capped/sealed flexible tube may maintain a substantially vertical alignment as biopsy device (10) is rotated +/−90° about the longitudinal axis defined by needle (20) during a process of obtaining a plurality of tissue samples (e.g., during a single insertion of needle (20) within a patient, etc.). Having excess fluids substantially remain within the capped/sealed flexible tube as biopsy device (10) is rotated in such a fashion may substantially reduce the likelihood of such fluids contacting hydrophobic filter (48).

As yet another merely illustrative variation, auxiliary vacuum source (400) may be omitted, and a hydrophilic member (not shown) may be positioned within outer cup (44) to soak up liquids communicated proximally through cutter lumen (52). Such a hydrophilic member may swell and reduce the effective internal volume of outer cup (44) as the hydrophilic member absorbs liquids, which may in turn allow vacuum pump (38) to generate and maintain a vacuum within outer cup (44) more easily. Other suitable arrangements of components for biopsy system (1000) will be apparent to those of ordinary skill in the art in view of the teachings herein.

It should also be understood that fluid canister (300) and auxiliary vacuum source (400) may be integrated together in a single device (e.g., such that conduit (340) is omitted, etc.). An example of a vacuum source with integrated fluid canister is described in U.S. Pub. No. 2008/0214955, entitled "Presentation of Biopsy Sample by Biopsy Device," published Sep. 4, 2008, the disclosure of which is incorporated by reference herein. Other suitable ways in which fluid canister (300) and auxiliary vacuum source (400) may be integrated together will be apparent to those of ordinary skill in the art.

It should be understood from the foregoing that fluid canister (300) and/or auxiliary vacuum source (400) may be coupled with biopsy device (10) and/or otherwise be used before a biopsy procedure is initiated, during a biopsy procedure (e.g., on an "as needed" basis), or at any other suitable time.

Exemplary Pneumatic Operation

As noted above, vacuum pump (38) and/or auxiliary vacuum source (400) is/are operable to induce a vacuum in tissue sample holder (40), and such vacuum may be further communicated to cutter lumen (52). In particular, vacuum pump (38) and/or auxiliary vacuum source (400) may start building a vacuum in cutter lumen (52) as soon as motor (36) is activated; and such a vacuum may continue to build or be maintained as cutter (50) starts moving proximally toward the retracted position. At this stage, second lumen (28) is vented to atmosphere. In particular, shuttle valve slider (152) is in a distal position, allowing atmospheric air to reach second lumen (28)—via openings (208), notches (153), the gap between the inner diameter of shuttle valve slider (152) and the outer diameter of cutter (50), and the portion of sleeve interior (206) that is distal to shuttle valve slider (152). Alternatively, second lumen (28) may be fluidly coupled with vacuum pump (38) and/or auxiliary vacuum source (400), such that a vacuum is created in second lumen (28) at this stage.

As cutter (50) moves toward retracted position, such that lateral aperture (24) of needle (20) is "partially open," a vacuum in cutter lumen (52) may be further communicated through first lumen (26), which may draw tissue into lateral aperture (24). At this stage, second lumen (28) is still vented to atmosphere. In particular, due to the "lost motion" between cutter (50) and shuttle valve slider (152), shuttle valve slider (152) remains in the distal position despite proximal retraction of cutter (50). Alternatively, second lumen (28) may be fluidly coupled with vacuum pump (38) and/or auxiliary vacuum source (400), such that a vacuum is created in second lumen (28) at this stage.

When cutter (50) reaches the fully retracted position, such that lateral aperture (24) of needle (20) is "open", a vacuum in cutter lumen (52) may continue to be further communicated through first lumen (26), which may continue to draw tissue into lateral aperture (24). Of course, some amount of tissue may naturally prolapse into lateral aperture (24) without the assistance of vacuum, such that vacuum may not even be needed to draw tissue into lateral aperture (24). At this stage, second lumen (28) is substantially sealed relative to atmosphere. In particular, stop member (55) has pushed shuttle valve slider (152) to a proximal position, such that o-rings (210) "straddle" openings (208) and seal against the interior sidewall of sleeve portion (204) to prevent atmospheric air from being communicated from openings (208) to second lumen (28) via hollow interior (206) of sleeve portion (204).

As motor (36) is reversed and cutter (50) is advanced to sever tissue protruding through lateral aperture (24), vacuum pump (38) and/or auxiliary vacuum source (400) may continue to induce a vacuum in cutter lumen (52), and second lumen (28) may eventually be vented to atmosphere. However, in the initial stages of advancement of cutter (50) from the proximal-most position to the distal-most position, the "lost motion" between cutter (50) and shuttle valve slider (152) leaves shuttle valve slider (152) in the proximal position until cutter (50) advances far enough for the distal end of sleeve (250) to engage the proximal end of shuttle valve slider (152). Until such engagement between the distal end of sleeve (250) and the proximal end of shuttle valve slider (152), o-rings (210) of shuttle valve slider (152) continue to substantially seal second lumen (28) from openings (208). After the distal end of sleeve (250) engages the proximal end of shuttle valve slider (152), and after cutter (50) has continued to move distally to a sufficient degree, the distal end of sleeve (250) eventually pushes shuttle valve slider (152) distally, such that the proximal-most o-ring (210) is eventually moved distal to openings (208). With shuttle valve slider (152) reaching such a position (and positions that are further distal to such a position), second lumen (28) is again vented to atmosphere as described above. As cutter (50) again finally reaches the distal-most position, cutter (50) may completely sever the tissue protruding through lateral aperture (24), with second lumen (28) being vented.

With the severed tissue sample residing in cutter lumen (52), with vacuum pump (38) and/or auxiliary vacuum source (400) drawing a vacuum at the proximal face of the severed tissue sample, and with the venting being provided at the distal face of the severed tissue sample (via openings (208), second lumen (28), and openings (27)), the pressure differential applied to the severed tissue sample may cause the severed tissue sample to be drawn proximally through cutter lumen (52) and into upper chamber (43a) of tissue sample holder (40). The severed tissue sample may thus be deposited on collection tray (46) of tissue sample holder (40); or on a screen positioned above collection tray (46) in tissue sample holder (40). Any fluids drawn through cutter lumen (52) into outer cup (44) of tissue sample holder (40) may flow through port (49), through conduit (320), and into cup (302) of fluid canister (300). Alternatively (e.g., in versions where fluid canister (300) is omitted), fluids drawn through cutter lumen (52) into outer cup (44) of tissue sample holder (40) may simply remain in outer cup (44) until outer cup (44) is emptied.

Of course, any other suitable structures, components, configurations, or techniques may be used to provide selective sealing and/or venting of second lumen (28). By way of example only, while shuttle valve slider (152) is actuated mechanically based on the axial position of cutter (50) in the present example, it should be understood that shuttle valve slider (152) or any other type of valve may instead be actuated electrically (e.g., via a separate motor or solenoid), pneumatically, or otherwise. Furthermore, in some variations of biopsy device (10), a vacuum, saline, pressurized air, atmospheric air, and/or any other medium may be communicated to second lumen (28) at any suitable stage of operation of biopsy device (10) (e.g., applying vacuum or venting to second lumen (28) during and/or upon retraction of cutter (50) and/or during advancement of cutter (50), sealing second lumen during advancement of cutter (50), etc.). Suitable alternative structures, components, configurations, or techniques for communicating severed tissue samples proximally through cutter lumen (52) to reach tissue sample holder (40) will be apparent to those of ordinary skill in the art in view of the teachings herein.

Exemplary Method of Operation

In a merely exemplary use of biopsy device (10), a user first inserts tissue piercing tip (22) into the breast of a patient. During such insertion, cutter (50) may be advanced to the distal-most position, such that lateral aperture (24) of needle (20) is closed. As also noted herein, such insertion may be performed under visual guidance, stereotactic guidance, ultrasound guidance, MRI guidance, PEM guidance, BSGI guidance, palpatory guidance, some other type of guidance, or otherwise. With needle (20) sufficiently inserted into the patient's breast, the user may then activate motor (36), which may in turn activate vacuum pump (38) and cutter actuation mechanism (100). The user may also activate auxiliary vacuum source (400) at this stage and/or at a later stage in the procedure. Such activation of vacuum pump (38) and/or auxiliary vacuum source (400) may induce a vacuum in tissue sample holder (40) and cutter lumen (52) as described above. Such activation of cutter actuation mechanism (60) may cause cutter (50) to rotate counterclockwise and translate proximally. As cutter (50) starts retracting and when cutter (50) reaches the retracted position, vacuum from vacuum pump (38) and/or auxiliary vacuum source (400) (as communicated through tissue sample holder (40) and cutter lumen (52)) may draw tissue into lateral aperture (24) of needle (20). During this time, second lumen (28) may be vented by valve mechanism (150).

Once cutter (50) reaches a proximal-most position, vacuum may still be communicated through vacuum lumen (52) and first lumen (26), drawing tissue into lateral aperture (24) of needle (20). Second lumen (28) may be substantially sealed by valve assembly (150) at this time. In addition, lead screw (122) freewheels yet is biased distally by spring (128) as cutter (50) continues to rotate counterclockwise. Lateral aperture (24) is fully open at this stage, with tissue prolapsed therein.

The rotation direction of motor (36) is then reversed and cutter (50) begins to advance distally until again reaching the distal-most position. As cutter (50) advances distally, vacuum is still being communicated through vacuum lumen (52), helping to hold tissue in place as sharp distal edge (51) of cutter (50) begins to sever the tissue. Second lumen (28) is initially substantially sealed by valve assembly (150) at this time, but is eventually vented. Cutter (50) then reaches the distal-most position, thereby "closing" lateral aperture (24), and such that sharp distal edge (51) of cutter (50) completely severs the tissue. Vacuum is still being communicated through cutter lumen (52) at this time, and valve assembly (150) vents second lumen (28). As described above, this combination of vacuum and venting provides communication of the severed tissue sample proximally through cutter lumen (52) and onto collection tray (46) of tissue sample holder (40). Motor (36) may continue to operate at the end of the cutting stroke, thereby continuing to drive vacuum pump (38) to maintain a vacuum in tissue sample holder (40). Vacuum may also be maintained in tissue sample holder (40) at this stage by auxiliary vacuum source (400). In addition, spring (130) biases lead screw (122) proximally to engage threads (132), while allowing cutter (50) to continue rotating at the distal-most position. A cutting stroke will thus be complete, and may be initiated as many times as desired to acquire additional tissue samples.

As noted above, several cutting strokes may be performed to acquire several tissue samples without the user having to withdraw needle (20) from the patient's breast. The user may adjust the orientation of lateral aperture (24) about the axis defined by needle (20) by rotating the entire biopsy device (10) between cutting strokes for multiple sample acquisition. Alternatively, biopsy device (10) may be configured such that needle (20) is rotatable relative to body (30), such that needle (20) may be rotated via a thumbwheel or other feature. Once the desired number of tissue samples have been obtained, the user may withdraw needle (20) from the patient's breast. The user may then remove cap (42) from cup (44) and retrieve the tissue samples from collection tray (46).

At the end of a procedure, the user may separate probe (12) from holster (14). Holster (14) may then be cleaned and/or sterilized for subsequent use. Probe (12) may be disposed of. Alternatively, as noted above, biopsy device (10) may alternatively be formed as a unitary construction, such that there is no probe (12) separable from a holster (14).

Of course, the above examples of use of biopsy device (10) are merely illustrative. Other suitable ways in which biopsy device (10) may be used will be apparent to those of ordinary skill in the art in view of the teachings herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:
1. A biopsy system comprising:
 (a) a biopsy device, wherein the biopsy device comprises:
  (i) a body,
  (ii) a needle extending distally from the body,

(iii) a hollow cutter movable relative to the needle to sever a tissue sample, wherein the hollow cutter defines a cutter lumen,
(iv) a primary vacuum pump located within the body, wherein the primary vacuum pump is operable to induce a vacuum in the cutter lumen, wherein the primary vacuum pump is operable to draw a vacuum proximally through the cutter lumen, and
(v) a motor operable to drive the primary vacuum pump and the hollow cutter;
(b) a fluid canister in communication with the biopsy device, wherein the fluid canister is configured to receive liquids communicated proximally through the cutter lumen; and
(c) an auxiliary vacuum source in communication with the biopsy device, wherein the auxiliary vacuum source is operable to induce a vacuum in the cutter lumen.

2. The biopsy system of claim 1, wherein the auxiliary vacuum source is coupled with the fluid canister, such that the auxiliary vacuum source is in fluid communication with the cutter lumen via the fluid canister.

3. The biopsy system of claim 2, wherein the fluid canister comprises a cup portion and a lid portion, wherein the lid portion comprises a first port coupling the auxiliary vacuum source with the cup portion, wherein the lid portion further comprises a second port coupling the cup portion with the biopsy device.

4. The biopsy system of claim 2, further comprising a first flexible conduit coupling the fluid canister with the biopsy device and a second flexible conduit coupling the auxiliary vacuum source with the fluid canister.

5. The biopsy system of claim 1, wherein the motor is operable to simultaneously drive both the hollow cutter and the primary vacuum pump.

6. The biopsy system of claim 5, wherein the motor is located on or within the body of the biopsy device.

7. The biopsy system of claim 1, wherein the biopsy device further comprises a tissue sample holder configured to receive tissue samples communicated proximally through the cutter lumen, wherein the tissue sample holder extends proximally from the body.

8. The biopsy system of claim 7, wherein the tissue sample holder is integral with the body of the biopsy device, wherein the tissue sample holder extends proximally from the body of the biopsy device.

9. The biopsy system of claim 7, wherein the primary vacuum pump, the fluid canister, and the auxiliary vacuum source are all in fluid communication with the tissue sample holder, such that the primary vacuum pump and the auxiliary vacuum source are operable to induce a vacuum in the cutter lumen via the tissue sample holder, and such that the fluid canister is configured to receive liquids communicated proximally through the cutter lumen via the tissue sample holder.

10. The biopsy system of claim 9, further comprising a first hydrophobic filter and a second hydrophobic filter, wherein the first hydrophobic filter is configured to substantially isolate the primary vacuum pump from liquids communicated to the tissue sample holder while permitting the primary vacuum pump to induce a vacuum in the cutter lumen via the tissue sample holder, wherein the second hydrophobic filter is configured to substantially isolate the auxiliary vacuum source from liquids communicated to the fluid canister while permitting the auxiliary vacuum source to induce a vacuum in the cutter lumen via the tissue sample holder.

11. A biopsy system comprising:
(a) a biopsy device, wherein the biopsy device comprises:
(i) a body,
(ii) a needle extending distally from the body,
(iii) a hollow cutter movable relative to the needle to sever a tissue sample, wherein the hollow cutter defines a cutter lumen,
(iv) a primary vacuum pump located on or within the body, wherein the primary vacuum pump is operable to induce a vacuum in the cutter lumen and
(v) a tissue sample holder configured to receive tissue samples communicated proximally through the cutter lumen, wherein the tissue sample holder is in a fluid path of communication between the hollow cutter and the primary vacuum pump;
(b) a first flexible conduit in fluid communication with the cutter lumen; and
(c) a fluid canister coupled with the first flexible conduit, wherein the fluid canister is separate from the body of the biopsy device, wherein the fluid canister is configured to receive liquids communicated proximally through the cutter lumen via the first flexible conduit; and
(d) an auxiliary vacuum source in communication with the biopsy device, wherein the auxiliary vacuum source is operable to induce a vacuum in the cutter lumen.

12. The biopsy system of claim 11, further comprising a second flexible conduit in fluid communication with the cutter lumen, wherein the auxiliary vacuum source is coupled with the second flexible conduit.

13. The biopsy system of claim 12, wherein the second flexible conduit is further coupled with the fluid canister, such that the auxiliary vacuum source is operable to induce a vacuum in the cutter lumen via the first and second flexible conduits and via the fluid canister.

14. The biopsy system of claim 11, further comprising at least one hydrophilic member, wherein the at least one hydrophilic member is positioned in one or both of the biopsy device or the fluid canister, wherein the at least one hydrophilic member is configured to substantially soak up liquids.

15. A biopsy system comprising:
(a) a biopsy device, wherein the biopsy device comprises:
(i) a body,
(ii) a needle extending distally from the body,
(iii) a hollow cutter movable relative to the needle to sever a tissue sample, wherein the hollow cutter defines a cutter lumen, and
(iv) a primary vacuum pump located within the body, wherein the primary vacuum pump is operable to induce a vacuum in the cutter lumen, wherein the primary vacuum pump is in fluid communication with a tissue sample holder, wherein the tissue sample holder extends proximally from the body; and
(b) an auxiliary vacuum source in communication with the biopsy device, wherein the auxiliary vacuum source is operable to induce a vacuum in the cutter lumen.

16. The biopsy system of claim 15, further comprising a fluid canister in communication with the biopsy device, wherein the fluid canister is configured to receive liquids communicated proximally through the cutter lumen.

17. The biopsy system of claim 16, further comprising a first flexible conduit in fluid communication with the cutter lumen, wherein the fluid canister is coupled with the first flexible conduit, wherein the fluid canister is separate from the body of the biopsy device, wherein the fluid canister is configured to receive liquids communicated proximally through the cutter lumen via the first flexible conduit.

18. The biopsy system of claim 15, further comprising a second flexible conduit in fluid communication with the cutter lumen, wherein the auxiliary vacuum source is separate from the body of the biopsy device, wherein the auxiliary vacuum source is coupled with the second flexible conduit such that the auxiliary vacuum source is operable to induce a vacuum in the cutter lumen via the second flexible conduit.

19. The biopsy system of claim 15, wherein the biopsy device further comprises an integral tissue sample holder in fluid communication with the cutter lumen, wherein the tissue sample holder contains a hydrophilic member, wherein the hydrophilic member is configured to substantially soak up liquids communicated proximally through the cutter lumen to the tissue sample holder.

* * * * *